(12) United States Patent
Kaplan

(10) Patent No.: US 6,193,577 B1
(45) Date of Patent: Feb. 27, 2001

(54) ALTERNATIVE MEDICINE ELEMENTS PACKAGE

(76) Inventor: Mira S. Kaplan, 25 Colby Ct., Pleasanton, CA (US) 94566

( * ) Notice: Subject to any disclaimer, the term of this patent is extended or adjusted under 35 U.S.C. 154(b) by 0 days.

(21) Appl. No.: 09/397,798

(22) Filed: Sep. 17, 1999

(51) Int. Cl.$^7$ ........................................ A63H 3/36
(52) U.S. Cl. .................... 446/72; 446/73; 446/129; 446/369; 446/374; 446/385; 600/15
(58) Field of Search ................. 446/71–76, 369, 446/385, 374, 268, 129; 600/9, 15

(56) References Cited

U.S. PATENT DOCUMENTS

| | | | |
|---|---|---|---|
| 3,808,418 | * | 4/1974 | Conard et al. . |
| 3,977,121 | * | 8/1976 | Goldfarb et al. . |
| 4,136,484 | * | 1/1979 | Abrams . |
| 4,169,336 | * | 10/1979 | Kuhn . |
| 4,204,110 | * | 5/1980 | Smit et al. . |
| 4,606,328 | * | 8/1986 | Thoman . |
| 4,954,118 | * | 9/1990 | Tefabert . |
| 4,968,281 | * | 11/1990 | Smith et al. . |
| 5,071,385 | * | 12/1991 | Cox . |
| 5,362,271 | * | 11/1994 | Butt . |
| 5,516,314 | * | 5/1996 | Anderson . |
| 5,807,112 | * | 9/1998 | Zeck . |
| 5,807,155 | * | 9/1998 | Divvleeon . |
| 6,030,274 | * | 2/2000 | Kaplan . |

* cited by examiner

Primary Examiner—Jacob K. Ackun
Assistant Examiner—Jeffrey D. Carlson
(74) Attorney, Agent, or Firm—H. Michael Brucker

(57) ABSTRACT

An alternative medicine elements package in which a soft sculpture doll having a body portion and at least two arm-like appendages attached to the body portion includes a magnet in each of the arm-like appendages and a copper strip that extends through the body portion and into each of the arm-like appendages.

3 Claims, 3 Drawing Sheets

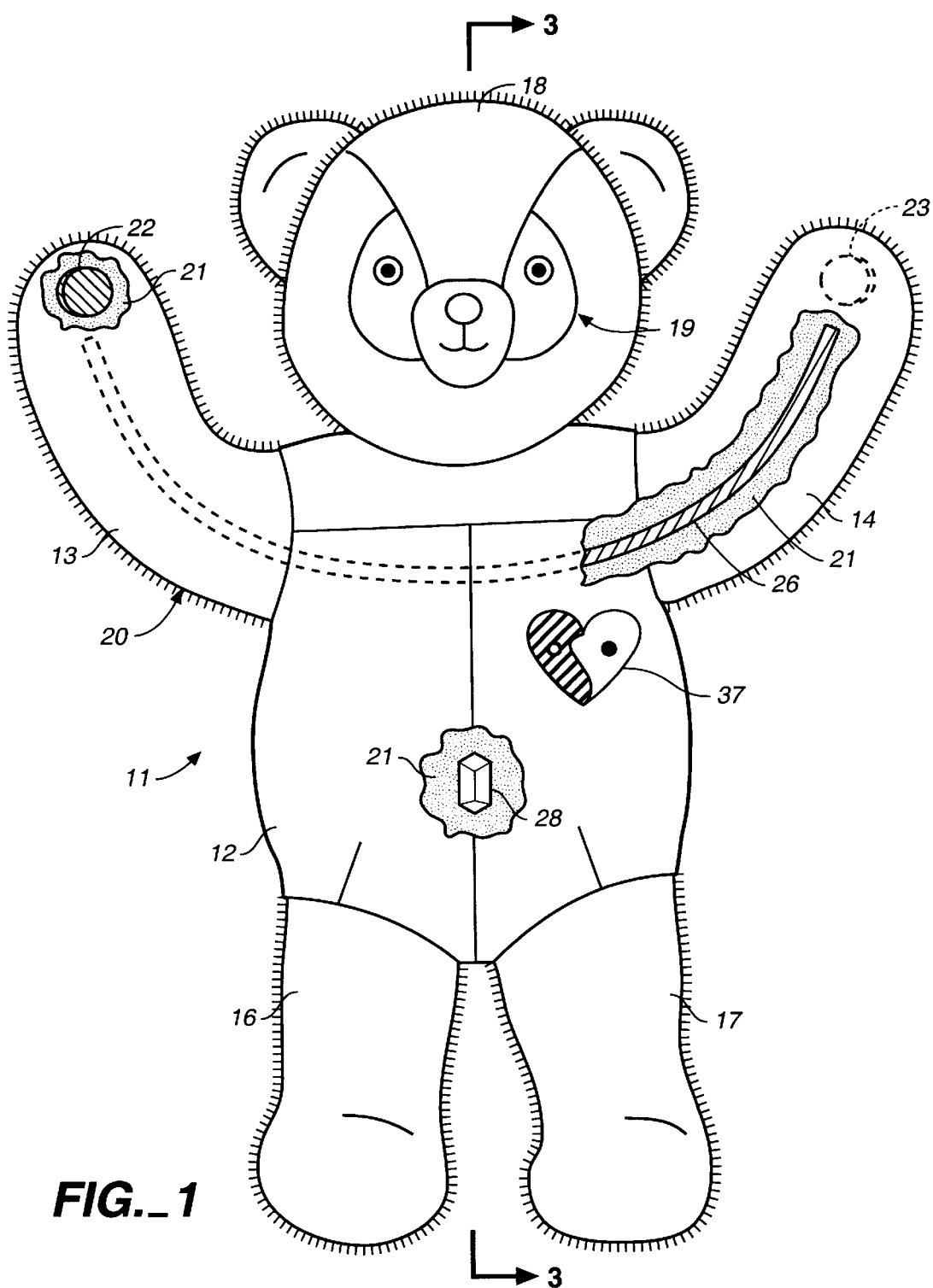
FIG._1

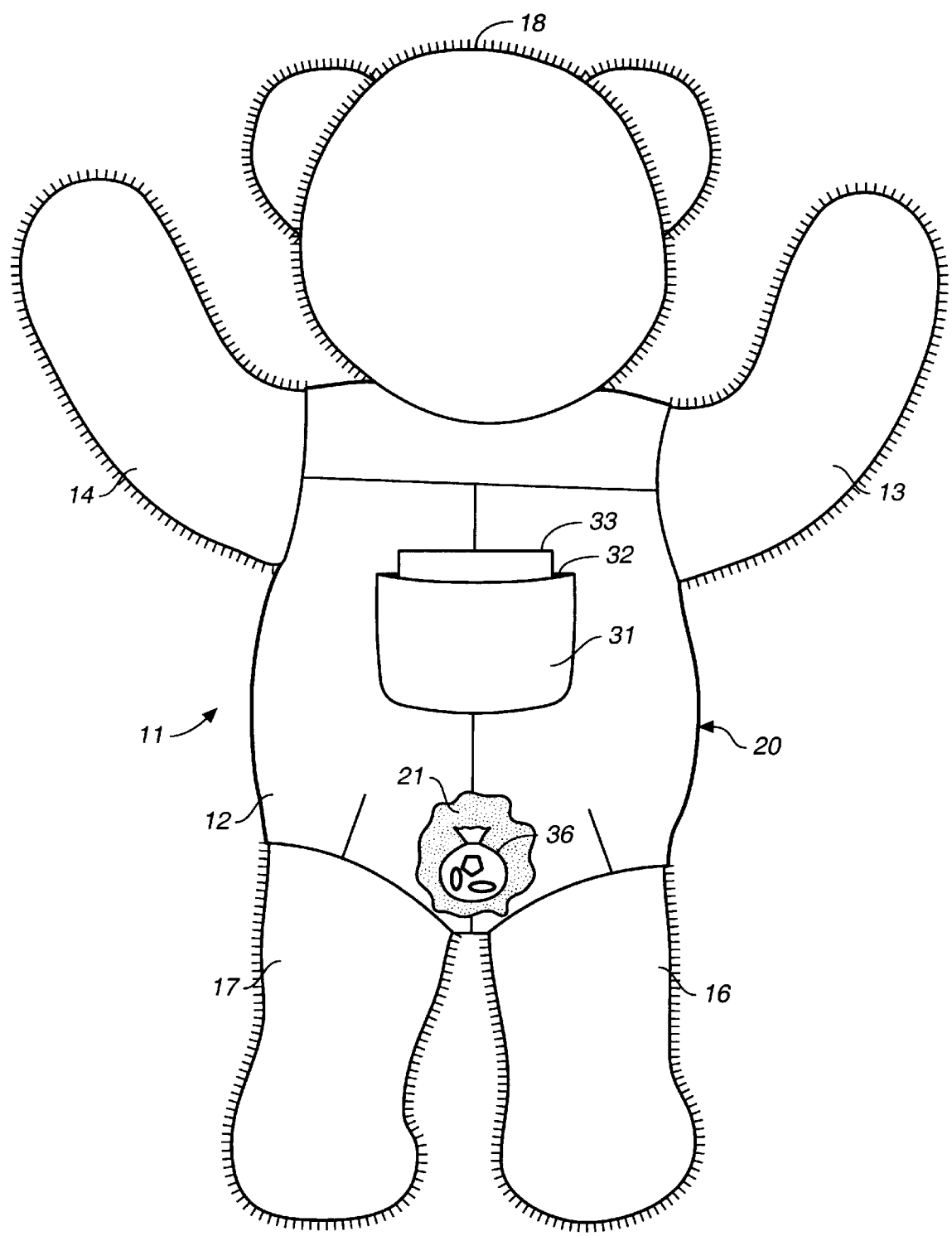
FIG._2

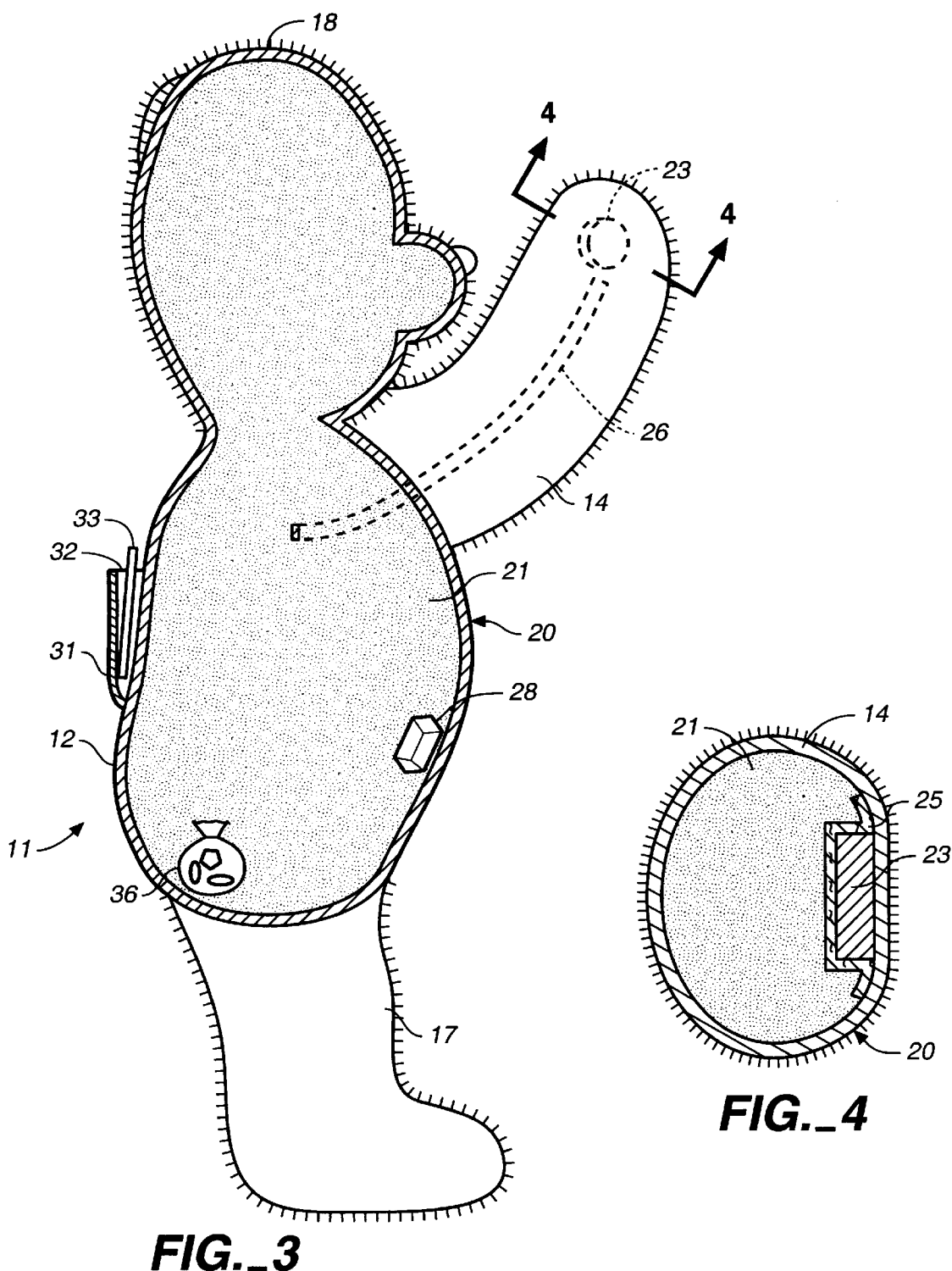
FIG._3
FIG._4

ALTERNATIVE MEDICINE ELEMENTS PACKAGE

The present invention relates to an alternative medicine elements package and, more particularly, to a plurality of alternative medicine elements carried by and embedded in a soft sculpture, the appearance of which is designed to engender feelings of affection and comfort.

The following definitions are used herein:

Allopathic medicine—Mainstream conventional western medical practices.

Alternative healing practice—A healing practice other than conventional western (allopathic) approaches.

Alternative medicine—Healing practices other than conventional western (allopathic) approaches.

Alternative healing elements—Physical objects used in connection with various alternative healing practices.

Aromatherapy—An ancient healing art in which essential oils from herbs and flowers are applied to the skin or inhaled to address physical, emotional and spiritual imbalances.

Holistic—Healing practices that consider the mind, body and spirit and appropriately integrate many traditions of healing as they apply to the individual person and situation.

Soft sculpture doll—an object formed by an outer skin of cloth or cloth-like material forming an enclosure which is filled with pliable material. It may be in the form of an animal or person or other object, either real or imaginary.

While not formally recognized according to standards of allopathic medicine as having healing powers, there are a number of alternative healing practices for promoting health and well being that trace their roots deep into human history. More and more people are turning to these ancient practices and more and more investigations are discovering their power. The effectiveness of these holistic healing practices is said to be enhanced by, and in some cases dependant upon, receiving their powers with an open heart—a feeling of love and affection.

The invention will be described with reference to the following alternative healing practice elements:

Crystals and glass beads—Healers of many cultures have used crystals, gemstones, glass beads, minerals and metals for thousands of years. Crystals are prized for their beauty, and certainly their color and appearance can affect mood. Crystals—both natural and glass—are thought to have the ability to amplify and focus energy into the environment. The ancient Chinese art of Feng Shui recommends special placement of crystals and mirrors when decorating homes for the purpose of creating a healing, harmonious environment.

Copper—The use of copper and other metals for healing dates back for many centuries, and in many cultures, copper is known to be a strong transmitter of energy. Native Americans used copper for healing, and today, many healers advise wearing copper jewelry such as bracelets. Nowadays, copper cuffs are being worn by many professional sports figures because many people believe that wearing copper affords natural, safe lessening of inflammation and pain. Some people believe that copper affects the emotions and brings in love, affection, harmony, beauty and peace.

Magnets—In China, India, Egypt and Greece, magnets have been used for healing for more than 4,000 years. Today, magnets are increasingly used and accepted to speed pain relief and healing, and improve circulation and general health. Magnetic wave therapy is said to fortify, balance and unblock the stagnant energy within our bodies. Reportedly, the natural healing process is enhanced with the application of magnetic fields to injured areas, increasing blood flow and oxygen exchange.

Herbs and Aromatherapy scents—Aromatherapy is an increasingly popular, gentle, fun, relaxing method of healing that uses specific natural aromas to help balance the mind, body and spirit. Essential oils of herbs, flowers, plants, trees and spices are used to create that balance. The practice of aromatherapy dates back thousands of years to ancient Egypt, India and China.

Many of the healing practices with which these elements are used fall into a category that can be termed "energy healing." They are subtle but believed by many to be potentially powerful inputs that interact with the energy system of the body to stabilize emotional, physical, mental and spiritual states. To many people, these interactions are seen as helping assist wellness and healing on all levels.

While the invention will be described with reference to the particular elements described above, those skilled in the art will recognize that other elements could also be used without departing from the invention.

It is an object of the present invention to provide an alternative medicine package of healing elements that helps promote an emotional state thought best for receiving the powers of the packaged elements.

It is a further object of the invention to so package the elements that they are hidden from view and protected from physical harm.

These and other objects of the invention are achieved by locating a plurality of alternative healing elements in a soft sculpture in the form of an object or animal that engenders the feelings of love and comfort. In the preferred embodiment, the soft sculpture doll is a teddy bear, or puppy, or kitten or the like, which children and adults all over the world have long used as highly personal objects of affection, love and comfort. The invention will be described with reference to a bear as the soft sculpture package for the elements. However, when the word "bear" is used, it is meant to represent any soft sculpture that could function to both contain and support the elements and engender feelings of openness and acceptance.

The invention serves as a vehicle for remembering and revisiting forgotten wisdom of the ages. This wisdom can be layered and intertwined with new thought, as well as with conventional allopathic medical practice, to yield a new, wonderful hybrid wellness program.

The bears can be taken on an inner or outer personal journey. Their size makes them perfect for taking on trips or just staying at home. They can fit into a suitcase or travel on an airplane or join in meditation or watching television. They can be taken for walks, out to dance, and out to eat in a restaurant. They can enter the world of dreams during sleep. They may provide comfort and some solutions in the echo of words spoken to them. The bear will always listen without criticizing or judging.

BRIEF DESCRIPTION OF THE DRAWINGS

FIG. 1 is a front perspective view of the invention in the form of a soft sculpture bear with parts broken away to reveal internal elements;

FIG. 2 is a rear perspective view of the invention of FIG. 1 with parts broken away to reveal internal elements;

FIG. 3 is a sectional view taken along the line 3—3 of FIG. 1; and

FIG. 4 is a sectional view taken along the line 4—4 of FIG. 3.

DESCRIPTION OF THE INVENTION

Referring to the Figures, a soft sculpture doll 11 in the form of a bear has a body portion 12 to which are connected arm-like appendages 13 and 14 and leg-like appendages 16 and 17. The body also carries a head portion 18. While the embodiment of the invention illustrated is in the form of a bear, the invention is not so limited. The representational qualities of doll 11 can be altered by changing the face portion 19 to give the appearance of some other animal. It is not, however, necessary that doll 11 represent an animal or any known creature, whether real or imaginary, since one of the purposes of soft sculpture doll 11 is to engender feelings of affection and comfort. Thus, the variations are limited only by imagination. In the preferred embodiment of the invention, however, the body portion has at least two arm-like appendages 13 and 14.

Soft sculpture doll 11 is formed in a manner well known in the arts and, in particular, a number of separate pattern pieces are sewn together to form an outer skin 20, which is then filled with stuffing material 21. A variety of different stuffing materials well known in the art are used for soft sculpture dolls, including natural and synthetic fibers. The invention is not limited either by the stuffing material or outer skin material, which can vary depending on the effect desired.

Disposed below the outer covering material 20 in internal pockets 25 toward the distal end of arms 13 and 14 are magnets 22 and 23, respectively (FIG. 4).

A copper strip 26 is disposed within the interior of the soft sculpture doll 11 and, in the preferred embodiment, the strip 26 extends from the body portion 12 into the arm-like appendages 13 and 14. The strip 26 is malleable, and thus, when the arms are bent into a desired shape, they will tend to stay in that shape. Thus, it is possible to place the magnets 22 and 23 around a desired location of the body or at a desired location of the body following the body contours by positioning the arm-like appendages 13 and 14. In this way, the magnets 22 and 23, as well as the copper strip 26, are jointly able to be focused on a particular area of the human anatomy.

At the mid section of the body portion 12 (what anatomically would be the location of the naval if the soft sculpture doll body represents the body of an animal or a human) is a crystal 28 disposed beneath the skin material 20 where it is protected by the surrounding stuffing material 21. Although not shown, the crystal 28 could also be enclosed within a pocket structure.

An exterior pouch or pocket 31 having an open end 32 is formed on the back of the body 12. The pouch 31 provides a receptacle for a packet 33. The packet 33 can contain scented herbs or aromatherapy fragrances as desired.

The herbs are provided for inhalation purposes. Since herbal aromas are very mild, they offer a gentle way of experiencing herbs. The herbs may be combined with aromatherapy elements in removable, replaceable packets 33 contained in the back pocket 31. The herbs are selected to achieve a specified mood and therapeutic benefit.

Aromatherapy is intended to be mild and, as with herbs, aromatherapy fragrances may be incorporated into the removable, replaceable packet 33 in the back of the bear. The scent, either from aromatherapy fragrance or herbs, imbues the bear with a subtle, pleasant aroma that can alter mood. Pressing lightly on the bear's back or gently shaking the bear may stimulate the release of more fragrance.

Disposed within the body portion 12 beneath the skin material 20 is a container 36 of glass beads or gemstones as desired. Once again, the container 36 is held within the body portion 12 and surrounded by stuffing material 21 so as to protect the contents.

The objectives of the invention, including engendering feelings of affection and comfort, can be enhanced by the selection of outer skin materials, color and the presence of symbols, such as the yin-yang symbol 37 illustrated in FIG. 1.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A package for containing alternative healing elements used in connection with alternative, holistic, healing practices for promoting health and well being comprising in combination:

a soft sculpture doll having a body portion and at least two arm-like appendages for containing alternative healing elements whereby the healing elements can be used simultaneously;

an alternative healing element crystal contained within said body portion;

an alternative healing element copper strip disposed within said body portion and extending into two of said arm-like appendages; and an alternative healing element magnet disposed near the distal end of each of said arm-like appendages into which said cooper strip extends.

2. The package of claim 1 further comprising:

a pocket on the exterior of said body portion containing aromatherapy materials.

3. The alternative medicine package of claim 2 further comprising:

an alternative healing element packet of glass beads disposed within said body portion.

* * * * *